(12) United States Patent
Naughton (10) Patent No.: US 6,284,284 B1
(45) Date of Patent: Sep. 4, 2001

(54) COMPOSITIONS AND METHODS FOR PRODUCTION AND USE OF AN INJECTABLE NATURALLY SECRETED EXTRACELLULAR MATRIX

(75) Inventor: Gail K. Naughton, La Jolla, CA (US)

(73) Assignee: Advanced Tissue Sciences, Inc., La Jolla, CA (US)

( * ) Notice: Subject to any disclaimer, the term of this patent is extended or adjusted under 35 U.S.C. 154(b) by 0 days.

(21) Appl. No.: 09/182,822

(22) Filed: Oct. 29, 1998

Related U.S. Application Data (60) Division of application No. 08/660,787, filed on Jun. 6, 1996, which is a continuation-in-part of application No. 08/470,101, filed on Jun. 6, 1995, now Pat. No. 5,830,708.

(51) Int. Cl.[7] ............................ A61K 35/12; A01N 37/18
(52) U.S. Cl. ............................ 424/520; 424/572; 514/21; 514/801
(58) Field of Search .................... 514/21, 801; 424/520, 424/572

(56) References Cited

U.S. PATENT DOCUMENTS

| | | |
|---|---|---|
| 3,949,073 | 4/1976 | Daniels et al. . |
| 4,424,208 | 1/1984 | Wallace et al. . |
| 4,582,640 | 4/1986 | Smedstad et al. . |
| 4,721,096 | 1/1988 | Naughton et al. . |
| 4,801,299 | 1/1989 | Brendel et al. . |
| 4,803,075 | 2/1989 | Wallace et al. . |
| 4,837,285 | 6/1989 | Berg et al. . |
| 4,963,489 | 10/1990 | Naughton et al. . |
| 5,002,071 | 3/1991 | Harrell et al. . |
| 5,032,508 | 7/1991 | Naughton et al. . |
| 5,160,490 | 11/1992 | Naughton et al. . |
| 5,204,382 | 4/1993 | Wallace et al. . |
| 5,266,480 | 11/1993 | Naughton et al. . |
| 5,288,617 | 2/1994 | Mattick et al. . |
| 5,342,765 | 8/1994 | Irvine et al. . |
| 5,397,352 | 3/1995 | Burres et al. . |
| 5,443,950 | 8/1995 | Naughton et al. . |
| 5,460,939 | 10/1995 | Hasbrough et al. . |
| 5,478,739 | 12/1995 | Slivka et al. . |
| 5,516,532 | 5/1996 | Atala et al. . |
| 5,541,106 | 7/1996 | Jones et al. . |
| 5,716,394 | 2/1998 | Brchman et al. . |

FOREIGN PATENT DOCUMENTS

| | | |
|---|---|---|
| 0 466 105 A2 | 1/1992 | (EP) . |
| WO 95/31944 | 11/1995 | (WO) . |
| WO 96/08213 | 3/1996 | (WO) . |
| WO 96/39101 | 12/1996 | (WO) . |

OTHER PUBLICATIONS

Dell'Orbo et al., 1992, Arch. Histol. Cytol. 55(3):235–241, "The dependency of collagen fibrillogenesis in vitro on fibroblast culture conditions. Fibroblasts in Mono– and multi–layers."

Gospodarowicz et al., 1981, "Factors controlling the proliferative rate, final cell density, and life span of bovine vascular smooth muscle cells in culture", J. Cell Biol 89:568–578.

Gralnick et al, 1977, "Factor V111", Ann. Int. Med. 86:598–616.

Larson et al., 1987, "Junctional transfer of small molecules in culture bovine brain microvascular endothelial cells and pericytes", Microvascular Res. 34:184–199.

Naughton et al., 1987, "Hematopoiesis on nylon mesh template", J. Med. 18 (3+4):219–250.

Nusgens et al., 1984, Coll. Relat. Res. 4(5):351–363 "Collagen biosynthesis by cells in a tissue equivalent matrix in vitro."

Oliver et al., 1980, "Effect of aldehyde cross–liinking on human dermal collagen implants in the rat", Br. J. Exp. Path. 61:544–549.

Oliver et al., 1976, "Histological studies of subcutaneous and intraperitoneal implants of trypsin–prepared dermal collagen allografts in the rat", Clin. Orth. Rel. Res. 115:291–302.

Oliver et al., 1981, Hydroxyproline turnover in dermal collagen grafts in reconstructed skin wounds in the rat, Conn. Tissue Res. 9:59–62.

Orange, 1992, "Findings suggest latent reaction to silicone injections may occur", Skin and Allergy News 23 (No 6):1.

Ponten and Westermark, 1980, "Cell generation and aging of nontransformed glial cells from adult humans", in Federof, Hertz, eds., Advances in Cell. Neuro. vol. 1, New York Academic Press, pp. 209–227.

Schechter et al., 1975, "Prolonged Retention of Glutaraldehyde–treated skin homografts in humans", Br. J. Plastic Surg. 28:198–202.

*Primary Examiner*—Christina Y. Chan
*Assistant Examiner*—Karen Clemens
(74) *Attorney, Agent, or Firm*—Pennie & Edmonds LLP (57) ABSTRACT

The present invention discloses compositions containing natural human extracellular matrices and methods for the use thereof. More particularly, the present invention provides compositions and methods for the repair of skin defects using natural human extracellular matrix by injection.

16 Claims, 5 Drawing Sheets

COMPOSITIONS AND METHODS FOR PRODUCTION AND USE OF AN INJECTABLE NATURALLY SECRETED EXTRACELLULAR MATRIX

This application is a divisional application of U.S. patent application Ser. No. 08/660,787 filed Jun. 6, 1996, which is a continuation-in-part application of U.S. patent application Ser. No. 08/470,101 filed Jun. 6, 1995, now U.S. Pat. No. 5,830,708, which are each incorporated by reference herein in their entirety.

INTRODUCTION

The present invention relates to compositions and methods for the treatment and repair of soft tissue and skin defects such as wrinkles and scars. More particularly, the invention relates to an injectable composition of human extracellular matrix components and methods of preparing and using same. The injectable preparation is obtained from three-dimensional living stromal tissues that are prepared in vitro.

BACKGROUND OF THE INVENTION

The idea of using an injectable material for soft tissue augmentation and repair developed soon after the invention of the hypodermic needle. Various products have been injected into the human body for correction of soft tissue and skin defects including paraffin, petrolatum, vegetable oils, lanolin, bees wax, and silicone. Injectable liquid silicone has been used extensively, however, due to long term side effects, such as nodules, recurring cellulitis and skin ulcers which are now being followed more closely, the use of injectable silicone is on the decline. Further, in the State of Nevada it is a felony to use injectable silicone in a human. Orange, Skin and Allergy News (1992) Vol.23, No.6, pg. 1. More recently, bovine collagen has gained widespread use as an injectable material for soft tissue augmentation. Collagen is the principal extracellular structural protein of the animal body. At least fourteen types of mammalian collagen have been described. The common characteristic amongst them is a three stranded helix, consisting of three polypeptide chains, called alpha-chains. All alpha-chains have the same configuration, but differ in the composition and sequence of their amino acids. Although this leads to different types of alpha-chains, however, they all have glycine at every third position in the amino acid sequence. The glycine at every third position allows for the helical structure of the alpha-chains. Type I collagen is composed of two $alpha_1$-chains and one $alpha_2$-chain and is the principal extracellular material of skin, tendon and bone. When clinicians mention "collagen", they are usually referring to type I collage n. See Table I, infra, for a detailed listing of collagen types I–V and in which tissues they are found.

Collagen has been used as an implant material to replace or augment hard or soft connective tissue, such as skin, tendon, cartilage, bone and interstitium. Additionally, collagen implants have been used for cosmetic purposes for a number of years since collagen can help cellular ingrowth at the placement site. Early collagen implants were often solid collagen masses which were cross-linked with chemical agents, radiation or other means to improve mechanical properties, decrease immunogenicity and/or increase resistance to resorption. The collagen utilized was in a variety of forms, including cross-linked and non-cross-linked fibrillar collagens, gelatins, and the like and sometimes was combined with various other components, such as lubricants, osteogenic factors and the like, depending on use. A major disadvantage of solid cross-linked collagen implants is the requirement for surgical implantation by means of incision. In addition, lack of deformability and flexibility are other disadvantages of solid collagen implants.

Oliver et al., Clinical Orthopaedics & Related Research (1976) 115:291–302; Br. J. Exp. Path. (1980) 61:544–549; and Conn. Tissue Res. (1981) 9:59–62 describe implants made by treating skin with trypsin followed by cross-linking with an aldehyde. The resulting solid collagen implants were reported to maintain their original mass after prolonged implantation. A main problem with such solid implants is that they must be implanted surgically. Other disadvantages are that they are not as deformable as injectable implants and residual glutaraldehyde may cause the implant to lose its flexibility due to continuing cross-linking in situ.

Schechter, et al., Br. J. Plas. Surg. (1975) 28:198–202 disclose glutaraldehyde cross-linked skin that was soaked in L-alanine after cross-linking. The article postulates that the exposure of the skin to L-alanine blocked residual reactive groups of the aldehyde, thereby preventing the release of toxic molecules generated by such groups.

An alternative to surgically implanted solid collagen material is disclosed in U.S. Pat. Nos. 3,949,073. 3,949,073 describes the use of atelopeptide solutions of bovine collagen as an injectable implant material for augmenting soft tissue. According to the patent, the bovine collagen is reconstituted before implantation and forms a fibrous mass of tissue when implanted. The patent suggests adding particles of insoluble bovine collagen microfibrils to control the shrinkage of the fibrous mass formed at the augmentation site. The commercial embodiment of the material described in the patent is composed of reconstituted atelopeptide bovine collagen in saline that contains a small amount of local anesthetic. While effective, the implant shrinks in volume after implantation due primarily to absorption of its fluid component by the body. Thus, if volume consistency is essential, an additional injection or injections of supplemental implant material is required. This specific composition has many serious drawbacks, e.g., the collagen is from a bovine source, not human, and the preparation process is not only lengthy and expensive but also requires the addition of microfibrils.

U.S. Pat. No. 4,424,208 describes an injectable dispersion of cross-linked atelopeptide bovine collagen and reconstituted atelopeptide bovine collagen fibers in an aqueous carrier which exhibited improved volume consistency over the material of U.S. Pat. No. 3,949,073.

U.S. Pat. No. 4,582,640 discloses an improved injectable implant over U.S. Pat. Nos. 3,949,073 and 4,424,208 in which the improvement consists of improved volume consistency and resistance to physical deformation, improved injectability as compared to the dispersion of U.S. Pat. No. 4,424,208 and that the bovine collagen contains only a single physical form of collagen as compared to the two physical forms found in U.S. Pat. No. 4,424,208.

U.S. Pat. No. 4,803,075 describes bovine collagen compositions including a lubricant material to enhance injectability through narrow diameter needles for soft tissue repair.

Despite the advantages and overall usefulness of the injectable collagen implant materials disclosed above, problems associated with producing and injecting the materials have been encountered. For example, for soft tissue repair, suspensions of fibrillar collagen have often been used by injecting the composition to a treatment site through a fine gauge needle. The use of fibrillar collagen as the primary matrix material in injectable soft and hard tissue implant compositions has several limitations. The preparation of fibrillar collagen suitable for human use is relatively time consuming and expensive. In particular, the complete removal of contaminating and potentially immunogenic substances to produce atelocollagen is a relatively complex and expensive procedure. Moreover, the persistence, shape retention, cohesiveness, stability, elasticity, toughness and intrudability of the fibrillar collagen compositions are not optimal.

In addition to the problems associated with producing and injecting the collagen implant materials, problems with the actual use of the above mentioned patented injectable implants are also abundant. For instance, since the above patented injectables derive collagen from xenogeneic sources, usually bovine collagen, the collagen must be modified to reduce its immunogenicity. Even with modified collagen, the implant material is still quite immunogenic to which some people are either already naturally allergic or develop an allergic reaction over time to the bovine collagen. Due to these allergic reactions the injectable collagen implants described above cannot be given to many people and others are limited to receiving only three injections per year. Severe allergic reactions include symptoms of rheumatoid arthritis, while less severe reactions include redness and swelling at the site of injection which may lead to permanent scarring. Because of these severe side effects, the above described collagen injectables are no longer used for lip augmentation. Further, the problems associated with injecting xenogeneic collagen seem so intractable that rather than injecting collagen, biocompatible ceramic matrices have been injected to achieve similar results as described in U.S. Pat. No. 5,204,382.

In summary, due to the shortcomings of the above-described injectable compositions for the repair of soft tissue defects, such as the lack of persistence, the need for repeated injections and serious concern over adverse reactions, newer injectable materials for soft tissue augmentation are needed.

SUMMARY OF THE INVENTION

The present invention relates to injectable materials for soft tissue augmentation and methods for use and manufacture of the same, which overcome the shortcomings of bovine injectable collagen and other injectable materials, including silicone, of the prior art. The injectable materials used in accordance with the present invention comprise naturally secreted extracellular matrix preparations as well as preparations derived from naturally secreted extracellular matrix. These preparations are biocompatible, biodegradable and are capable of promoting connective tissue deposition, angiogenesis, reepithilialization and fibroplasia, which is useful in the repair of skin and other tissue defects. These extracellular matrix preparations may be used to repair tissue defects by injection at the site of the defect.

The injectable preparations of the present invention have many advantages over conventional injectable collagen preparations used for the repair of skin defects. The extracellular matrix preparations of the present invention contain only human proteins, therefore, there is a reduced risk of an immune response due to foreign proteins or peptides, especially the type of immune response seen with bovine collagen found in conventional injectable collagen preparations. Additionally, the injected preparations of the present invention should persist longer and even if multiple injections are required, the injections should not be subject to the "no more than three injections per year" rule of bovine collagen-based preparations due to the lack of immunogenicity. Another advantage provided by the present invention is that the preparations of native extracellular matrix contain a mixture of extracellular matrix proteins which closely mimics the compositions of physiologically normal conditions, for example, in an extracellular matrix derived from dermal cells, type I and III collagens, hyaluronic acid as well as various glycosaminoglycans and natural growth factors are present. Many of these extracellular matrix proteins and growth factors have been studied extensively and have been shown to be critical for wound healing and tissue restoration.

In another aspect of the invention, the preparations can be used in highly improved systems for in vitro tissue culture. In this embodiment, naturally secreted extracellular matrix coated three-dimensional frameworks can be used to culture cells which require attachment to a support in order to grow but do not attach to conventional tissue culture vessels. In addition to culturing cells on a coated framework, the extracellular matrix secreted by the cells onto the framework can be collected and used to coat vessels for use in tissue culture. The extracellular matrix, acting as a base substrate, may allow cells normally unable to attach to conventional tissue culture dish base substrates to attach and subsequently grow.

Yet another embodiment of the present invention is directed to a novel method for determining the ability for cellular taxis of a particular cell. The method involves inoculating one end of a native extracellular matrix coated three-dimensional framework with the cell type in question and over time measure the distance traversed across the framework by the cell. Because the extracellular matrix is secreted naturally by the cells onto the framework, it is an excellent in vitro equivalent of extracellular matrix found in the body. Such an assay, for example, may inform whether isolated tumor cells are metastatic or whether certain immune cells can migrate across or even chemotact across the framework, thus, indicating that the cell has such cellular taxis ability.

DEFINITIONS AND ABBREVIATIONS

The following terms used herein shall have the meanings indicated:

Adherent Layer
    cells attached directly to the three-dimensional framework or connected indirectly by attachment to cells that are themselves attached directly to the matrix.

Pharmaceutically Acceptable Carrier
    an aqueous medium at physiological isotonicity and pH and may contain other elements such as local anesthetics and/or fluid lubricants.

Stromal Cells
    fibroblasts with or without other cells and/or elements found in loose connective tissue, including but not limited to, endothelial cells, pericytes, macrophages, monocytes, plasma cells, mast cells, adipocytes, chondrocytes, etc.

Three-Dimensional Framework
    a three dimensional support composed of any material and/or shape that (a) allows cells to attach to it (or can be modified to allow cells to attach to it); and (b) allows cells to grow in more than one layer. This support is inoculated with stromal cells to form the living stromal matrix.

Living Stromal Tissue a three dimensional framework which has been inoculated with stromal cells. Whether confluent or subconfluent, stromal cells according to the invention continue to grow and divide. The living stromal tissue prepared in vitro is the source of the extracellular matrix proteins used in the injectable formulations of the invention.

The following abbreviations shall have the meanings indicated:

EDTA ethylene diamine tetraacetic acid

FBS fetal bovine serum

HBSS Hank's balanced salt solution

HS horse serum

MEM minimal essential medium

PBS phosphate buffered saline

RPMI 1640 Roswell Park Memorial Institute Medium No. 1640 (GIBCO, Inc., Grand Island, N.Y.)

SEM scanning electron microscopy

The present invention may be more fully understood by reference to the following detailed description, examples of specific embodiments and appended figures which are offered for purposes of illustration only and not by way of limitation.

BRIEF DESCRIPTION OF THE FIGURES

FIG. 1.

FIG. 2A–D.

DETAILED DESCRIPTION OF THE INVENTION

One embodiment of the present invention involves the preparation and use of an injectable extracellular matrix composition for the treatment of skin defects. The extracellular matrix proteins are derived from a living stromal tissue prepared in vitro by growing stromal cells on a three-dimensional framework resulting in a multi-layer cell culture system. In conventional tissue culture systems, the cells were grown in a monolayer. Cells grown on a three-dimensional framework support, in accordance with the present invention, grow in multiple layers, forming a cellular matrix. This matrix system approaches physiologic conditions found in vivo to a greater degree than previously described monolayer tissue culture systems. The three-dimensional cell culture system is applicable to the proliferation of different types of stromal cells and formation of a number of different stromal tissues, including but not limited to dermis, bone marrow stroma, glial tissue, cartilage, to name but a few.

In accordance with the present invention, the pre-established living stromal tissue comprises stromal cells grown on a three-dimensional framework or network. The stromal cells can comprise fibroblasts with or without additional cells and/or elements described more fully herein. The fibroblasts and other cells and/or elements that comprise the stroma can be fetal or adult in origin, and can be derived from convenient sources such as skin, liver, pancreas, etc. Such tissues and/or organs can be obtained by appropriate biopsy or upon autopsy. In fact, cadaver organs may be used to provide a generous supply of stromal cells and elements.

Once inoculated onto the three-dimensional framework, the stromal cells will proliferate on the framework, and elaborate growth factors, regulatory factors and extracellular matrix proteins that are deposited on the support. The living stromal tissue will sustain active proliferation of the culture for long periods of time. Growth and regulatory factors can be added to the culture, but are not necessary since they are elaborated by the stromal support matrix.

The naturally secreted extracellular matrix is collected from the three-dimensional framework and is processed further with a pharmaceutically acceptable aqueous carrier and placed in a syringe for precise placement of the biomaterial into tissues, such as the facial dermis.

The present invention is based, in part, on the discovery that during the growth of human stromal cells on a biodegradable or non-biodegradable three-dimensional support framework, the cells synthesize and deposit on the three-dimensional support framework a human extracellular matrix as produced in normal human tissue. The extracellular matrix is secreted locally by cells and not only binds cells and tissues together but also influences the development and behavior of the cells it contacts. The extracellular matrix contains various fiber-forming proteins interwoven in a hydrated gel composed of a network of glycosaminoglycan chains. The glycosaminoglycans are a heterogeneous group of long, negatively charged polysaccharide chains, which (except for hyaluronic acid) are covalently linked to protein to form proteoglycan molecules.

The fiber-forming proteins are of two functional types: mainly structural (collagens and elastin) and mainly adhesive (such as fibronectin and laminin). The fibrillar collagens (types I, II, and III) are rope-like, triple-stranded helical molecules that aggregate into long cable-like fibrils in the extracellular space; these in turn can assemble into a variety of highly ordered arrays. Type IV collagen molecules assemble into a sheetlike meshwork that forms the core of all basal laminae. Elastin molecules form an extensive cross-linked network of fibers and sheets that can stretch and recoil, imparting elasticity to the matrix. Fibronectin and laminin are examples of large adhesive glycoproteins in the matrix; fibronectin is widely distributed in connective tissues, whereas laminin is found mainly in basal laminae. By means of their multiple binding domains, such proteins help cells adhere to and become organized by the extracellular matrix.

As an example, a naturally secreted human dermal extracellular matrix contains type I and type III collagens, fibronectin, tenascin, glycosaminoglycans, acidic and basic FGF, TGF-α and TGF-β, KGF, decorin and various other secreted human dermal matrix proteins. As naturally secreted products, the various extracellular matrix proteins are produced in the quantities and ratios similar to that existing in vivo. Moreover, growth of the stromal cells in three dimensions will sustain active proliferation of cells in culture for much longer time periods than will monolayer systems. Further, the three-dimensional system supports the maturation, differentiation, and segregation of cells in culture in vitro to form components of adult tissues analogous to counterparts found in vivo. Thus, the extracellular matrix created by the cells in culture is more analogous to native tissues.

Although the applicants are under no duty or obligation to explain the mechanism by which the invention works, a number of factors inherent in the three-dimensional culture system may contribute to these features of the three dimensional culture system:

(a) The three-dimensional framework provides a greater surface area for protein attachment, and consequently, for the adherence of stromal cells.

(b) Because of the three-dimensionality of the framework, stromal cells continue to actively grow in contrast to cells in monolayer cultures, which grow to confluence, exhibit contact inhibition, and cease to grow and divide. The elaboration of growth and regulatory factors by replicating stromal cells may be partially responsible for stimulating proliferation and regulating differentiation of cells in culture.

(c) The three-dimensional framework allows for a spatial distribution of cellular elements which is more analogous to that found in the counterpart tissue in vivo.

(d) The increase in potential volume for cell growth in the three-dimensional system may allow the establishment of localized microenvironments analogous to native counterparts found in vivo.

(e) The three-dimensional matrix maximizes cell-cell interactions by allowing greater potential for movement of migratory cells, such as macrophages, monocytes and possibly lymphocytes in the adherent layer.

(f) It has been recognized that maintenance of a differentiated cellular phenotype requires not only growth/differentiation factors but also the appropriate cellular interactions. The present invention effectively recreates the stromal tissue microenvironment.

The three-dimensional stromal support, the culture system itself, and its maintenance, as well as various uses of the three-dimensional cultures and of the naturally secreted extracellular matrix are described in greater detail in the subsections below. Solely for ease of explanation, the detailed description of the invention is divided into the three sections, (i) growth of the three-dimensional stromal cell culture, (ii) isolation of the naturally secreted human extracellular matrix, and (iii) formulation of the isolated extracellular matrix into preparations for injection at the site of soft tissue defects.

Preparing the Living Stromal Tissue In Vitro

The three-dimensional support used to culture stromal tissue may be of any material and/or shape that:

(a) allows cells to attach to it (or can be modified to allow cells to attach to it); and (b) allows cells to grow in more than one layer.

A number of different materials may be used to form the framework, such as non-biodegradable or biodegradable materials. For example, non-biodegradable materials include but are not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE; teflon), thermanox (TPX), etc. Additionally, biodegradable material may also be utilized, including but not limited to: nitrocellulose, cotton, polyglycolic acid (PGA), cat gut sutures, cellulose, gelatin, dextran, collagen, chitosan, hyaluronic acid, etc. Any of these materials, bio- or non-biodegradable, can be woven into a mesh to form a three-dimensional framework. Alternatively, the materials can be used to form other types of three-dimensional frameworks, for example, sponges, such as collagen sponges.

Certain materials, such as nylon, polystyrene, etc., are poor substrates for cellular attachment. When these materials are used as the three-dimensional support framework, it is advisable to pre-treat the framework prior to inoculation of stromal cells in order to enhance the attachment of stromal cells to the framework. For example, prior to inoculation with stromal cells, nylon frameworks can be treated with 0.1 M acetic acid, and incubated in polylysine, FBS, and/or collagen to coat the nylon. Polystyrene can be similarly treated using sulfuric acid. A convenient nylon mesh which can be used in accordance with the invention is Nitex, a nylon filtration mesh having an average pore size of 210 $\mu$m and an average nylon fiber diameter of 90 $\mu$m (#3-210/36, Tetko, Inc., N.Y.).

Stromal cells comprising fibroblasts derived from adult or fetal tissue, with or without other cells and elements described below, are inoculated onto the framework. These fibroblasts may be derived from organs, such as skin, liver, pancreas, etc. which can be obtained by biopsy, where appropriate, or upon autopsy. In fact, fibroblasts can be obtained in quantity rather conveniently from any appropriate cadaver organ. In a preferred embodiment, fetal fibroblasts can be obtained in high quantity from foreskin.

Fibroblasts may be readily isolated by disaggregating an appropriate organ or tissue which is to serve as the source of the fibroblasts. This can be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, hyaluronidase, DNase, pronase, and/or dispase etc. Mechanical disruption can also be accomplished by a number of methods including, but not limited to the use of grinders, blenders, sieves, homogenizers, pressure cells, or insonators to name but a few. For a review of tissue disaggregation techniques, see Freshney, Culture of Animal Cells. A Manual of Basic Technique, 2d Ed., A.R. Liss, Inc., New York, 1987, Ch. 9, pp. 107–126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A.R. Liss, Inc., New York, 1987, Ch. 11 and 12, pp. 137–168.

The isolation of fibroblasts, for example, can be carried out as follows: fresh tissue samples are thoroughly washed and minced in Hanks' balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional framework, see Naughton et al., 1987, J. Med. 18(3&4):219–250. Inoculation of the three-dimensional framework with a high concentration of stromal cells, e.g., approximately $10^6$ to $5 \times 10^7$ cells/ml, will result in the establishment of the three-dimensional stromal support in shorter periods of time.

In addition to fibroblasts, other cells can be added to form the three-dimensional stromal cell culture-producing extracellular matrix. For example, other cells found in loose connective tissue may be inoculated onto the three-dimensional support framework along with fibroblasts. Such cells include, but are not limited to, endothelial cells, pericytes, macrophages, monocytes, plasma cells, mast cells, adipocytes, chondrocytes, etc. These stromal cells can be readily derived from appropriate organs such as skin, liver, etc., using methods known, such as those discussed above.

In one embodiment of the present invention, stromal cells which are specialized for the particular tissue to be cultured can be added to the fibroblast stroma for the production of a tissue type specific extracellular matrix. For example, dermal fibroblasts can be used to form the three-dimensional subconfluent stroma for the production of skin-specific extracellular matrix in vitro. Alternatively, stromal cells of hematopoietic tissue including, but not limited to, fibroblast endothelial cells, macrophages/monocytes, adipocytes and reticular cells, can be used to form the three-dimensional subconfluent stroma for the production of a bone marrow-specific extracellular matrix in vitro, see infra. Hematopoietic stromal cells can be readily obtained from the "buffy coat" formed in bone marrow suspensions by centrifugation at low forces, e.g., 3000×g. Stromal cells of liver may include fibroblasts, Kupffer cells, and vascular and bile duct endothelial cells. Similarly, glial cells can be used as the stroma to support the proliferation of neurological cells and tissues. Glial cells for this purpose can be obtained by trypsinization or collagenase digestion of embryonic or adult brain. Ponten and Westermark, 1980, In Federof, S. Hertz, L., eds, "Advances in Cellular Neurobiology," Vol.1, New York, Academic Press, pp.209–227.

For certain uses in vivo it is preferable to obtain the stromal cells from the patient's own tissues. The growth of cells in the presence of the three-dimensional stromal support framework can be further enhanced by adding to the framework, or coating the framework support with proteins, e.g., collagens, elastic fibers, reticular fibers, glycoproteins; glycosaminoglycans, e.g., heparin sulfate, chondroitin-4-sulfate, chondroitin-6-sulfate, dermatan sulfate, keratan sulfate, etc.; a cellular matrix, and/or other materials.

After inoculation of the stromal cells, the three-dimensional framework is incubated in an appropriate nutrient medium under physiologic conditions favorable for cell growth, i.e., promoting mitosis, i.e., cell division. Many commercially available media such as RPMI 1640, Fisher's, Iscove's, McCoy's, and the like may be suitable for use. It is important that the three-dimensional stromal culture be suspended or floated in the medium during the incubation period in order to maximize proliferative activity. In addition, the culture should be "fed" periodically to remove the spent media, depopulate released cells, and to add fresh media.

During the incubation period, the stromal cells will grow linearly along and envelop the three-dimensional framework before beginning to grow into the openings of the framework. The cells are grown to an appropriate degree to allow for adequate deposition of extracellular matrix proteins.

The openings of the framework should be of an appropriate size to allow the stromal cells to stretch across the openings. Maintaining actively growing stromal cells which stretch across the framework enhances the production of growth factors which are elaborated by the stromal cells, and hence, will support long term cultures. For example, if the openings are too small, the stromal cells may rapidly achieve confluence but be unable to easily exit from the mesh. Trapped cells can exhibit contact inhibition and cease production of the appropriate factors necessary to support proliferation and maintain long term cultures. If the openings are too large, the stromal cells are unable to stretch across the opening. This will also decrease stromal cell production of the appropriate factors necessary to support proliferation and maintain long term cultures. When using a mesh type of matrix, as exemplified herein, we have found that openings ranging from about 150 $\mu$m to about 220 $\mu$m will work satisfactorily. However, depending upon the three-dimensional structure and intricacy of the framework, other sizes may work equally well. In fact, any shape or structure that allows the stromal cells to stretch and continue to replicate and grow for lengthy time periods will work in accordance with the present invention.

Different proportions of the various types of collagen deposited on the framework can be achieved by inoculating the framework with different tissue-specific cells. For example, for hematopoietic cells, the matrix should preferably contain collagen types III, IV and I in an approximate ratio of 6:3:1 in the initial matrix. For skin, collagen types I and III are preferably deposited in the initial matrix. The proportions of collagen types deposited can be manipulated or enhanced by selecting fibroblasts which elaborate the appropriate extracellular matrix proteins. This can be accomplished using monoclonal antibodies of an appropriate isotype or subclass which are capable of activating complement, and which define particular collagen types. These antibodies in combination with complement can be used to negatively select the fibroblasts which express the desired collagen type. Alternatively, the stroma used to inoculate the framework can be a mixture of cells which synthesize the appropriate collagen types desired. The distribution and origins of the five types of collagen is shown in Table I.

TABLE I

DISTRIBUTIONS AND ORIGINS OF THE FIVE TYPES OF COLLAGEN

| Collagen Type | Principal Tissue Distribution | Cells of Origin |
| --- | --- | --- |
| I | Loose and dense ordinary connective tissue; collagen fibers | Fibroblasts and reticular cells; smooth muscle cells |
|  | Fibrocartilage |  |
|  | Bone | Osteoblast |
|  | Dentin | Odontoblasts |
| II | Hyaline and elastic cartilage | Chondrocytes Retinal Cells |
|  | Vitreous body of eye |  |
| III | Loose connective tissue; reticular fibers | Fibroblasts and reticular cells |
|  | Papillary layer of dermis Blood vessels | Smooth muscle cells; endothelial cells |

TABLE I-continued

DISTRIBUTIONS AND ORIGINS OF THE FIVE TYPES OF COLLAGEN

| Collagen Type | Principal Tissue Distribution | Cells of Origin |
|---|---|---|
| IV | Basement membranes | Epithelial and endothelial cells |
|  | Lens capsule of eye | Lens fibers |
| V | Fetal membranes; placenta Basement membranes Bone | Fibroblasts |
|  | Smooth muscle | Smooth muscle cells |

Thus, depending upon the collagen types desired, the appropriate stromal cell(s) can be selected to inoculate the three-dimensional framework.

The three-dimensional extracellular matrix producing culture of the present invention affords a vehicle for introducing gene products in vivo. In certain situations, it may be desirable to prepare an extracellular matrix containing a foreign gene product, growth factor, regulatory factor, etc. In such cases, the cells may be genetically engineered to express the gene product, or altered forms of the gene product that are immobilized in the extracellular matrix laid down by the stromal cells. For example, using recombinant DNA techniques, a gene of interest can be placed under the control of an inducible promoter. The recombinant DNA construct containing the gene can be used to transform or transfect a host cell which is cloned and then clonally expanded in the three-dimensional culture system. The use of the three-dimensional culture in this regard has a number of advantages. First, since the culture comprises eukaryotic cells, the gene product will be properly expressed and processed in culture to form an active product. Second, the number of transfected cells can be substantially enhanced to be of clinical value, relevance, and utility. The three-dimensional cultures of the present invention allow for expansion of the number of transfected cells and amplification (via cell division) of transfected cells.

Preferably, the expression control elements used should allow for the regulated expression of the gene so that the product can be over synthesized in culture. The transcriptional promoter chosen, generally, and promoter elements specifically, depends, in part, upon the type of tissue and cells cultured. Cells and tissues which are capable of secreting proteins (e.g., those characterized by abundant rough endoplasmic reticulum and golgi complex) are preferable.

During incubation of the three-dimensional culture, proliferating cells are released from the framework. These released cells can stick to the walls of the culture vessel where they can continue to proliferate and form a confluent monolayer. This should be prevented or minimized, for example, by removal of the released cells during feeding, or by transferring the three-dimensional framework to a new culture vessel. The presence of a confluent monolayer in the vessel will "shut down" the growth of cells in the three-dimensional framework and/or culture. Removal of the confluent monolayer or transfer of the stromal culture to fresh media in a new vessel will restore proliferative activity of the three-dimensional culture system. Such removal or transfers should be done in any culture vessel which has a stromal monolayer exceeding 25% confluency. Alternatively, the culture system can be agitated to prevent the released cells from sticking, or instead of periodically feeding the cultures, the culture system could be set up so that fresh media continuously flows through the system. The flow rate can be adjusted to both maximize proliferation within the three-dimensional culture, and to wash out and remove cells released from the matrix, so that they will not stick to the walls of the vessel and grow to confluence. In any case, the released stromal cells can be collected and crypreserved for future use.

Once inoculated onto the three-dimensional framework, adherence of the fibroblasts is seen quickly (e.g., within hours) and the fibroblasts begin to stretch across the framework openings within days. These fibroblasts are metabolically active, secrete extracellular matrix and rapidly form a dermal equivalent consisting of active fibroblasts and collagen.

Figure 1:
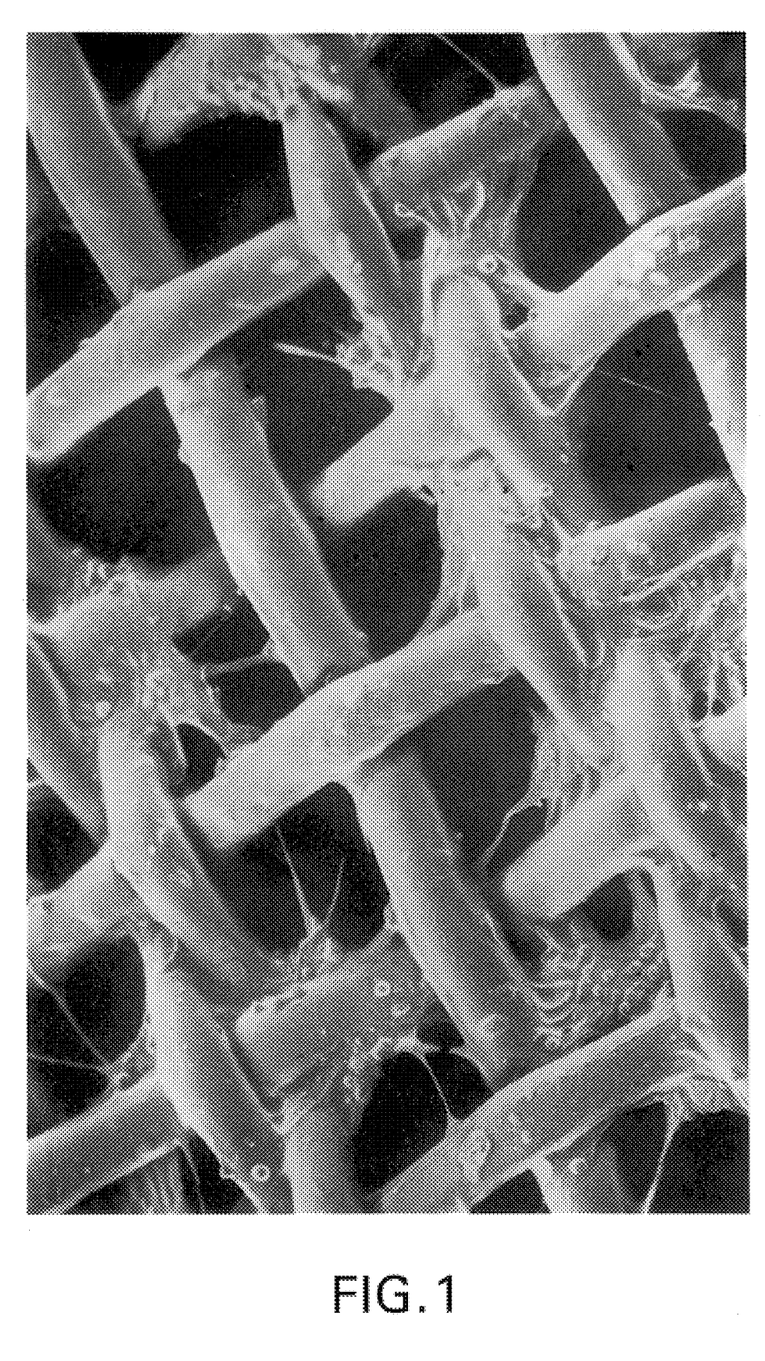
FIG. 1 is a scanning electron micrograph depicting fibroblast attachment to the three-dimensional matrix and extension of cellular processes across the mesh opening. Fibroblasts are actively secreting matrix proteins and are at the appropriate stage of subconfluency which should be obtained prior to inoculation with tissue-specific cells.
Figure 2A:
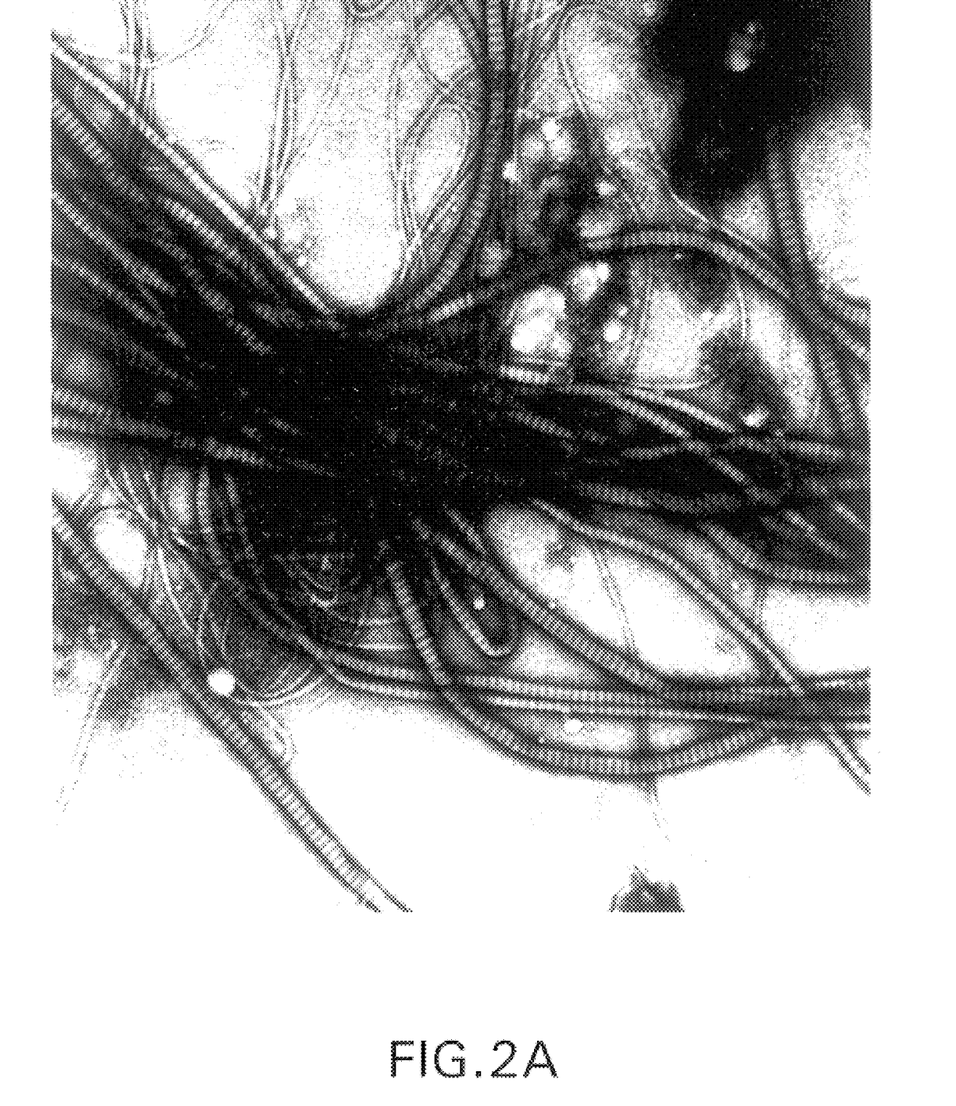
FIGS. 2A–D are transmission electron micrographs of collagen isolated from extracellular matrix prepared from dermal tissue grown in vitro (FIG. 2A–B) or from a normal adult human dermal sample (FIG. 2C–D).
Figure 2B:
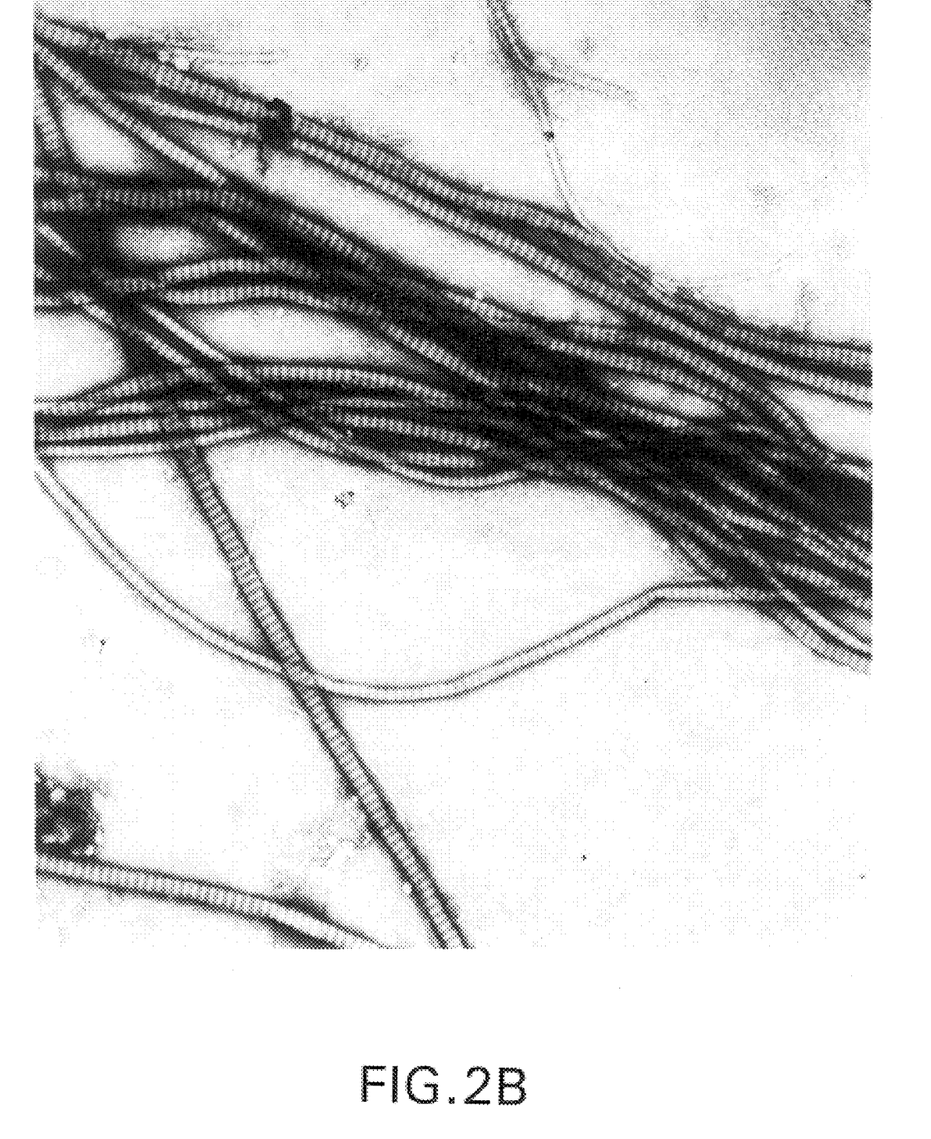
Figure 2C:
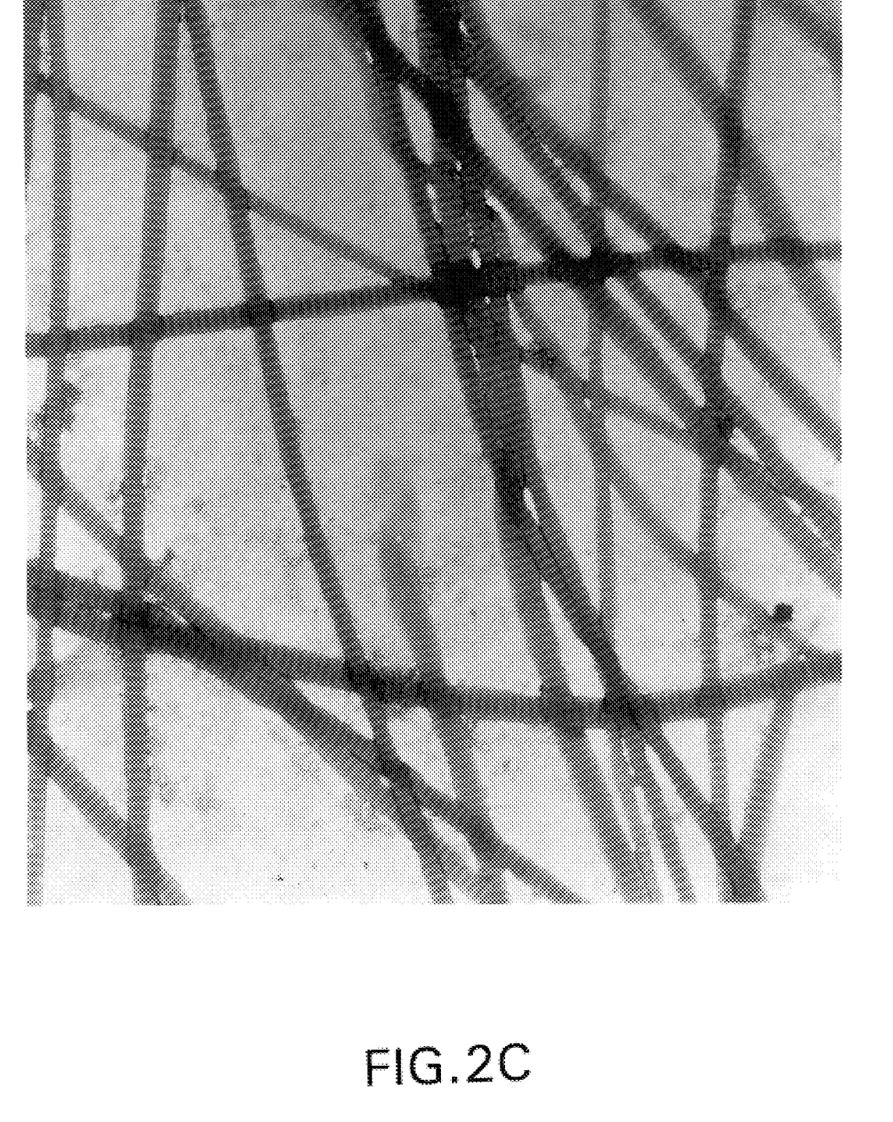
Figure 2D:
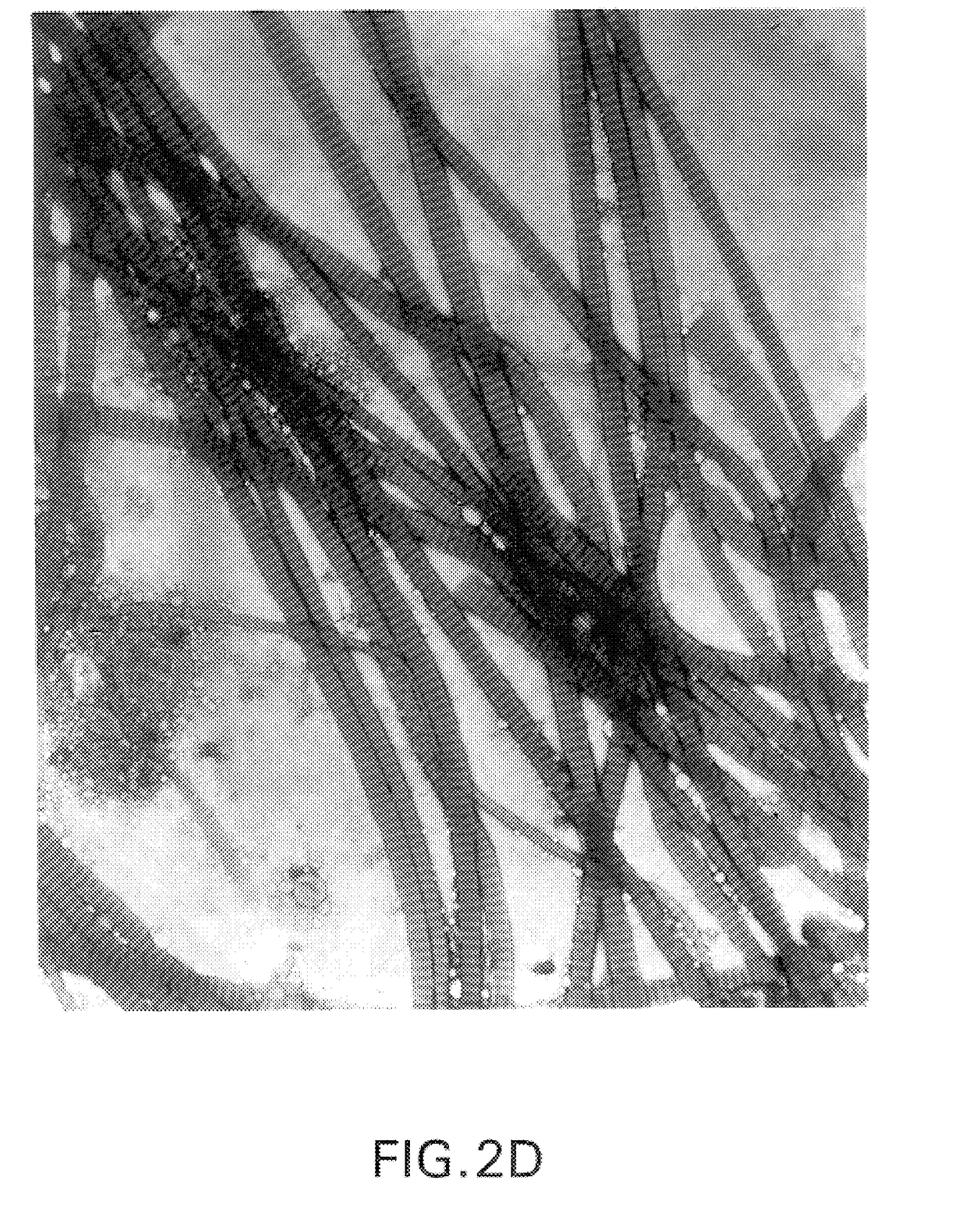

FIG. 1 illustrates the ability of the fibroblasts to arrange themselves into parallel layers between the naturally-secreted collagen bundles. These fibroblasts exhibit a rapid rate of cell division and protein secretion.

Removal of the Extracellular Matrix From the Framework

After the cells have been inoculated onto the framework and cultured under conditions favoring cellular growth, such that a desired amount of extracellular matrix is secreted on to the three-dimensional framework, the cells are killed and the naturally secreted extracellular matrix is processed further.

This involves first killing the cells and removing the killed cells and any cellular debris from the three-dimensional framework. This process is carried out in a number of different ways. For example, the cells can be killed by flash-freezing the living stromal tissue prepared in vitro in liquid nitrogen without a cryopreservative. Another way to kill the cells is to irrigate the inoculated three-dimensional framework with sterile water, such that the cells burst in response to osmotic pressure. Once the cells have been killed, one can, for example, disrupt the cellular membranes and remove the cellular debris by a mild detergent rinse, such as EDTA, CHAPS or a zwitterionic detergent, followed by treatment with a cryoprotectant such as DMSO, propylene glycol, butanediol, raffinose, polyvinyl pyrrolidone, dextran or sucrose and vitrified in liquid nitrogen. Alternatively, the framework can be subjected to enzymatic digestion and/or extracting with reagents that break down the cellular membranes and allow removal of cell contents. Examples of detergents include non-ionic detergents (for example, TRITON X-100, octylphenoxy polyethoxyethanol, (Rohm and Haas); BRIJ-35, a polyethoxyethanol lauryl ether (Atlas Chemical Co.), TWEEN 20, a polyethoxyethanol sorbitan monolaureate (Rohm and Haas), LUBROL-PX, or polyethylene lauryl ether (Rohm and Haas)); and ionic detergents (for example, sodium dodecyl sulphate, sulfated higher aliphatic alcohol, sulfonated alkane and sulfonated alkylarene containing 7 to 22 carbon atoms in a branched or unbranched chain). Enzymes can be used also and can include nucleases (for example, deoxyribonuclease and ribonuclease), phospholipases and lipases. An advantage to using a mild detergent rinse is that it will solubilize membrane-bound proteins, which are often highly antigenic.

Once the cells have been killed and the cellular debris has been removed, the collection of the naturally secreted human extracellular matrix can be accomplished in a variety of ways which depends on whether the three-dimensional framework is composed of material that is biodegradable or non-biodegradable. For example, if the framework is composed of non-biodegradable material, one can remove the extracellular matrix from a non-biodegradable support by subjecting the three-dimensional framework to sonication and/or to high pressure water jets and/or to mechanical scraping and/or to a mild treatment with detergents and/or enzymes to remove the attached extracellular matrix from the framework.

If the extracellular matrix is deposited on a biodegradable three-dimensional framework, after killing and removing the cells and cellular debris, the extracellular matrix can be recovered, for example, by simply allowing the framework to degrade in solution, i.e., allow the framework to dissolve, thus freeing the extracellular matrix. Additionally, if the biodegradable support is composed of a material which can be injected, like the extracellular matrix itself, one can process the entire extracellular matrix coated framework into syringes for injection. Further, if the extracellular matrix is deposited on a biodegradable support, the matrix can be removed by the same methods as if the matrix had been deposited on a non-biodegradable support, i.e., by subjecting the three-dimensional framework to sonication and/or to high pressure water jets and/or to mechanical scraping and/or to a mild treatment with detergents and/or enzymes to remove the attached extracellular matrix from the framework. None of the removal processes are designed to damage and/or denature the naturally secreted human extracellular matrix produced by the cells.

Formulation and Use of Injectable Preparations

Once the naturally secreted extracellular matrix has been collected, it is processed further. The extracellular matrix can be homogenized to fine particles, such that it can pass through a surgical needle. Homogenization is well known in the art, for example, by sonication. Further, the extracellular matrix can be cross-linked by gamma irradiation without the use of chemical cross-linking agents, such as glutaraldehyde, which are toxic. The gamma irradiation should be a minimum of 20 M rads to sterilize the material since all bacteria, fungi, and viruses are destroyed at 0.2 M rads. Preferably, the extracellular matrix can be irradiated from 0.25 to 2 M rads to sterilize and cross-link the extracellular matrix.

Further, the amounts and/or ratios of the collagens and other proteins may be adjusted by mixing extracellular matrices secreted by other cell types prior to placing the material in a syringe. For example, biologically active substances, such as proteins and drugs, can be incorporated in the compositions of the present invention for release or controlled release of these active substances after injection of the composition. Exemplary biologically active substances can include tissue growth factors, such as TGF-$\beta$, and the like which promote healing and tissue repair at the site of the injection.

Final formulation of the aqueous suspension of naturally secreted human extracellular matrix will typically involve adjusting the ionic strength of the suspension to isotonicity (i.e., about 0.1 to 0.2) and to physiological pH (i.e., about pH 6.8 to 7.5) and adding a local anesthetic, such as lidocaine, (usually at a concentration of about 0.3% by weight) to reduce local pain upon injection. The final formulation will also typically contain a fluid lubricant, such as maltose, which must be tolerated by the body. Exemplary lubricant components include glycerol, glycogen, maltose and the like. Organic polymer base materials, such as polyethylene glycol and hyaluronic acid as well as non-fibrillar collagen, preferably succinylated collagen, can also act as lubricants. Such lubricants are generally used to improve the injectability, intrudability and dispersion of the injected biomaterial at the site of injection and to decrease the amount of spiking by modifying the viscosity of the compositions. This final formulation is by definition the processed extracellular matrix in a pharmaceutically acceptable carrier.

The matrix is subsequently placed in a syringe or other injection apparatus for precise placement of the matrix at the site of the tissue defect. In the case of formulations for dermal augmentation, the term "injectable" means the formulation can be dispensed from syringes having a gauge as low as 25 under normal conditions under normal pressure without substantial spiking. Spiking can cause the composition to ooze from the syringe rather than be injected into the tissue. For this precise placement, needles as fine as 27 gauge (200$\mu$ I.D.) or even 30 gauge (150$\mu$ I.D.) are desirable. The maximum particle size that can be extruded through such needles will be a complex function of at least the following: particle maximum dimension, particle aspect ratio (length:width), particle rigidity, surface roughness of particles and related factors affecting particle:particle adhesion, the viscoelastic properties of the suspending fluid, and the rate of flow through the needle. Rigid spherical beads suspended in a Newtonian fluid represent the simplest case, while fibrous or branched particles in a viscoelastic fluid are likely to be more complex.

The above described steps in the process for preparing injectable naturally secreted human extracellular matrix are preferably carried out under sterile conditions using sterile materials. The processed extracellular matrix in a pharmaceutically acceptable carrier can be injected intradermally or subcutaneously to augment soft tissue, to repair or correct congenital anomalies, acquired defects or cosmetic defects. Examples of such conditions are congenital anomalies as hemifacial microsomia, malar and zygomatic hypoplasia, unilateral mammary hypoplasia, pectus excavatum, pectoralis agenesis (Poland's anomaly) and velopharyngeal incompetence secondary to cleft palate repair or submucous cleft palate (as a retropharyngeal implant); acquired defects (post-traumatic, post-surgical, post-infectious) such as depressed scars, subcutaneous atrophy (e.g., secondary to discoid lupis erythematosus), keratotic lesions, enophthalmos in the unucleated eye (also superior sulcus syndrome), acne pitting of the face, linear scleroderma with subcutaneous atrophy, saddle-nose deformity, Romberg's disease and unilateral vocal cord paralysis; and cosmetic defects such as glabellar frown lines, deep nasolabial creases, circum-oral geographical wrinkles, sunken cheeks and mammary hypoplasia. The compositions of the present invention can also be injected into internal tissues, such as the tissues defining body sphincters to augment such tissues.

Various sample embodiments of the invention are described in the sections below. For purposes of description only, and not by way of limitation, the three-dimensional culture system of the invention is described based upon the type of tissue and cells used in various systems. These descriptions specifically include but are not limited to bone marrow, skin, epithelial cells, and cartilage but it is expressly understood that the three-dimensional culture system can be used with other types of cells and tissues. The invention is also illustrated by way of examples, which demonstrate characteristic data generated for each system described.

EXAMPLES

Example: Three-dimensional Skin Stromal Culture System

The subsections below describe the three-dimensional culture system of the invention for culturing different stromal cells in vitro. Briefly, cultures of fibroblasts were established on nylon mesh which had been previously sterilized. Within 6–9 days of incubation, adherent fibroblasts began to grow into the meshwork openings and deposited parallel bundles of collagen. Indirect immunofluorescence using monoclonal antibodies showed predominantly type I collagen with some type III as well.

Establishment of the Three-dimensional Stroma of Skin Fibroblasts

Skin fibroblasts were isolated by mincing dermal tissue, trypsinization for 2 hours, and separation of cells into a suspension by physical means. Fibroblasts were grown to confluency in 25 cm$^2$ Falcon tissue culture dishes and fed with RPMI 1640 (Sigma, MO) supplemented with 10% fetal bovine serum (FBS), fungizone, gentamicin, and penicillin/streptomycin. Fibroblasts were lifted by mild trypsinization and cells were plated onto nylon filtration mesh, the fibers of which are approximately 90 $\mu$m in diameter and are assembled into a square weave with a mesh opening of 210 $\mu$m (Tetko, Inc., N.Y.). The mesh was pretreated with a mild acid wash and incubated in polylysine and FBS. Adherence of the fibroblasts was seen within 3 hours, and fibroblasts began to stretch across the mesh openings within 5–7 days of initial inoculation. These fibroblasts were metabolically active, secreted an extracellular matrix, and rapidly formed a dermal equivalent consisting of active fibroblasts and collagen. FIG. 1 is a scanning electron micrograph depicting fibroblast attachment and extension of cellular processes across the mesh opening.

Establishment of the Three-dimensional Bone Marrow Stromal Cultures

Bone marrow was aspirated from multiple sites on the posterior iliac crest of hematologically normal adult volunteers after informed consent was obtained. Specimens were collected into heparinized tubes and suspended in 8 ml of RPMI 1640 medium which was conditioned with 10% FBS and 20 5–10% HS and supplemented with hydrocortisone, fungizone, and streptomycin. The cell clumps were disaggregated and divided into aliquots of 5×10$^6$ nucleated cells.

Nylon filtration screen (#3-210/36, Tetko Inc., N.Y.) was used as a three-dimensional framework to support all stromal cell cultures described in the examples below. The screen consisted of fibers, which were 90 $\mu$m in diameter, assembled into a square weave pattern with sieve openings of 210 $\mu$m. Stromal cells were inoculated using the protocols described in Section 6.1. Adherence and subsequent growth of the stromal elements was monitored using inverted phase contrast microscopy and scanning electron microscopy (SEM).

Preparation of the Three-dimensional Oral Mucosal Epithelial Stromal Matrix

Samples of oral mucosal tissue were obtained from orthodontic surgical specimens. Tissue was washed three times with fresh MEM containing antibiotics (2 ml of antibiotic antimycotic solution from GIBCO, Cat. #600-5240 AG; and 0.01 ml of gentamicin solution from GIBCO Cat. #600-5710 AD per 100 cc MEM), cut into small pieces, then washed with 0.02% EDTA (w/v). 0.25% trypsin (in PBS without Ca$^{++}$ or Mg$^{++}$) was added; after a few seconds, the tissue pieces were removed and placed in fresh trypsin (in PBS without Ca$^{++}$ or Mg$^{++}$) and refrigerated at 4° C. overnight. Tissues were removed and placed in fresh trypsin solution, and gently agitated until cell appeared to form a single-cell suspension. The single-cell suspension was then diluted in MEM containing 10% heat inactivated fetal bovine serum and centrifuged at 1400×g for 7 minutes. The supernatant was decanted and the pellet containing mucosal epithelial cells was placed into seeding medium. Medium consisted of DMEM with 2% Ultrosen G, 1×L-glutamine, 1×nonessential amino acids, penicillin and streptomycin. The cells were seeded onto a three-dimensional framework. The three-dimensional stromal culture was generated using oral fibroblasts and 8 mm×45 mm pieces of nylon filtration screen (#3-210/36, Tetko Inc., N.Y.). The mesh was soaked in 0.1 M acetic acid for 30 minutes and treated with 10 mM polylysine suspension for 1 hour. The meshes were placed in a sterile petri dish and inoculated with 1×10$^6$ oral fibroblasts collected as described above in DMEM complete medium. After 1–2 hours of incubation at 5% $CO_2$ the meshes were placed in a Corning 25 cm$^2$ tissue culture flask, floated with an additional 5 ml of medium, and allowed to reach subconfluence, being fed at 3 day intervals. Cultures were maintained in DMEM complete medium at 37° C. and 5% $CO_2$ in a humidified atmosphere and were fed with fresh medium every 3 days.

Established of the Three Dimensional Small Vessel Endothelial Stromal Cell Culture Small vessel endothelial cells isolated from the brain according to the method of Larson et al., 1987, Microvasc. Res. 34:184 were cultured in vitro using T-75 tissue culture flasks. The cells were maintained in Dulbecco's Modified Eagle Medium/Hams-F-12 medium combination (the solution is available as a 1:1 mixture). The medium was supplemented with 20% heat-inactivated fetal calf serum (FCS), glutamine, and antibiotics. The cells were seeded at a concentration of 1×10$^6$ cells per flask, and reached a confluent state within one week. The cells were passaged once a week, and, in addition, were fed once a week with DMEM/Hams-F-12 containing FCS, glutamine, and antibiotics as described. To passage the cells, flasks were rinsed twice with 5 ml of PBS (without Ca$^{++}$ or Mg$^{++}$) and trypsinized with 3 ml of 0.05% Trypsin and 0.53 mM EDTA. The cells were pelleted, resuspended, and tested for viability by trypan blue exclusion, seeded and fed with 25 ml of the above mentioned DMEM/Hams-F-12 supplemented medium. A factor VIII related antigen assay, Grulnick et al., 1977, Ann. Int. Med. 86:598–616, is used to positively identify endothelial cells, and silver staining was used to identify tight junctional complexes, specific to only small vessel endothelium.

Nylon filtration screen mesh (#3-210/36, Tetko, Inc., N.Y.) was prepared essentially as described above. The mesh was soaked in an acetic acid solution (1 ml glacial acetic acid plus 99 ml distilled $H_2O$) for thirty minutes, was rinsed with copious amounts of distilled water and then autoclaved. Meshes were coated with 6 ml fetal bovine serum per 8×8 cm mesh and incubated overnight. The meshes were then stacked, three high, and 3×10$^7$ small vessel endothelial cells (cultured as described) were seeded onto the stack, and incubated for three hours at 37° C. under 5% $CO_2$ in a humidified atmosphere. The inoculated meshes were fed with 10 ml of DMEM/Hams-F-12 medium every 3–4 days until complete confluence was reached (in approximately two weeks).

Established of the Three Dimensional Chondrocyte Stromal Cell Culture

Cartilage was harvested from articular surfaces of human joints. The cartilage pieces were digested with collagenase (0.2% w/v) in complete medium (DMEM with 10% fetal bovine serum, glutamine, non-essential amino acids, sodium pyruvate, 50 μg/ml ascorbate and 35 μg/ml gentamicin) for 20 hours at 37° C. Liberated chondrocytes were spun, resuspended in complete medium, counted and plated at $1 \times 10^6$ cells per T-150 flask. Cells were routinely passed at confluence (every 5–7 days).

Polyglycolic acid mesh (1 mm diameter×2 mm thick) was sterilized by ethylene oxide or electron beam treatment and presoaked overnight in complete medium. The mesh was seeded in 6 well plates with $3-4 \times 10^6$ cells per mesh in a total volume of 10 μl and incubated for 3–4 hours at 37° C. in a tissue culture incubator. At this time, 1.5 ml of media was added. The seeded mesh was incubated overnight. 5 ml of media was added the next day. Media was changed three times per week until confluence is reached.

Example: Extracellular Matrix Composition

The extracellular matrix has been characterized by a number of analytic methods to determine its content of matrix proteins, each value is the average of at least two independent determinations. The matrix contained type I and type III collagens, fibronectin, tenascin, sulfated glycosaminoglycans, decorin and various other secreted human extracellular matrix proteins. Additionally, the secreted matrix proteins were found throughout the three-dimensional support framework. The extracellular matrix contained a total protein amount of 292 mg/cm$^2$±0.06; fibronectin was present at 3.4 mg/cm$^2$±1.2; and tenascin at 1.7 mg/cm$^2$±0.6. Both fibronectin and tenascin showed the expected molecular weight distributions on immunoblots.

Collagen Content of the Extracellular Matrix

Collagen content of the extracellular matrix was determined using the Sirius Red assay. The binding of Sirius Red F3BA in saturated picric acid solution has been used widely to estimate fibrotic collagen deposition. Bedossa et al., 1989, Digestion 44(1):7–13; Finkelstein et al., 1990, Br. J. Ophthalmol. 74(5):280–282; James et al., 1990, Liver 10(1):1–5. The specificity of Sirius Red binding to collagen is based largely on its use as a histological stain. In rat liver with various degrees of cholestatic fibrosis, collagen content measured by Sirius Red binding shows strong correlation with hydroxyproline content. Walsh et al., 1992, Analyt. Biochem. 203:187–190. In addition, histological staining with Sirius Red is birefringent, indicating directional binding related to the orientation of the collagen strands. Sirius Red is known to bind to proteins other than the classical collagens that contain collagen-like triple helices, such as the complement component C1. Some minor binding to serum albumin has also been found, although control experiments using bovine serum albumin standard showed no interference with the assay. The interference is estimated to represent less than 2% of the collagen signal in the extracellular matrix and the use of Sirius Red assay gives a reproducible method for measuring collagens. The extracellular matrix contained a collagen content of 0.61 mg/cm$^2$±0.09. Further, collagens I and III showed the expected molecular weight distributions on immunoblots.

Collagen Fibers Visualized Via Electron Microscopy

Collagen derived from the dermal tissue grown in vitro and collagen derived from a normal adult human dermal sample were processed and visualized by transmission electron microscopy (TEM). Briefly, the respective collagens were weighed and placed in a sterile 50 ml centrifuge tube with 30 ml 0.05 M Tris buffer, pH 8.0. After mixing for two hours on a wrist shaker, the Tris buffer was removed and the specimen placed in a homogenization cylinder along with 30 ml fresh 0.05 M Tris buffer. The sample was homogenized for 30 seconds in buffer alone and then for two 30 second bursts following the addition of a dispersing agent as described in U.S. Pat. Nos. 4,969,912 and 5,332,802. The temperature was maintained at 5–10° C. during the mechanical disruption process. The dispersing agent was added at a concentration of 0.05% (wet weight of the collagen). The homogenized preparation was centrifuged at 3500 rpm for 6 minutes to separate the dispersed collagenous material from the yet undispersed material. The undispersed residue was again treated with dispersing agent at 0.05% (wet weight of the collagen) and homogenized for two 30 second bursts. The dispersion was again centrifuged to recover dispersed collagenous material which was added to the first recovery.

The collagenous dispersion was filtered through a 100 micron filter, centrifuged at 3500 rpm and the pellet was washed 3 times with 0.004 M phosphate buffer, pH 7.4. The last centrifugation was conducted at 10,000 rpm to pack the collagenous pellet. Samples were then collected for TEM. As shown in FIGS. 2A–D, the collagen fibers isolated from either the extracellular matrix prepared from dermal tissue grown in vitro (FIGS. 2A–B) or from normal adult human dermis (FIGS. 2C–D) appeared identical in that intact collagen fibers with typical collagen banding and normal periodicity in both preparations.

Glycosaminoglycans Present in the Extracellular Matrix

Glycosaminoglycans have been shown to play a variety of structural and functional roles in the body and their presence in the secreted extracellular matrix is important. Table II lists a number of examples of glycosaminoglycans which have been determined to be found in the extracellular matrix as well as their functional importance in normal dermis.

TABLE II

| NAME | LOCATION | GLYCAN | FUNCTION | MECHANISM |
|---|---|---|---|---|
| Versican | Matrix | 12–15 Chondroitin sulfate | Structural | Binds hyaluronic acid and collagen |
| Decorin | Matrix | 1 Chondroitin/dermatan sulfate | Binding TGF-β and other growth factors; binds to collagen | Inactivates growth factors |

TABLE II-continued

| NAME | LOCATION | GLYCAN | FUNCTION | MECHANISM |
|---|---|---|---|---|
| Betaglycan | Cell membrane | 1–4 Chondroitin/heparan sulfate | TGF-β Type III receptor | Adjunct receptor for TGFβ |
| Syndecan | Cell membrane | 1–3 Chondroitin sulfate, 1–2 heparan sulfate | Growth factor binding | |

Further, the extracellular matrix was found to contain a total of 2.8 mg/cm$^2$±0.1 sulfated glycosaminoglycans.

Growth Factors Present in the Extracellular Matrix

The cells producing and depositing the extracellular matrix also expressed a number of different growth factors. Growth factors are important in the extracellular matrix for two reasons. During the growth of and deposition of the extracellular matrix, naturally seeded growth factors help to control cell proliferation and activity. Further, growth factors remain attached to the extracellular matrix. A variety of growth factors have been determined to be expressed during the deposition of the matrix.

The expression of growth factors has been examined by polymerase chain reaction of reverse transcripts (RT-PCR) of total RNA. Briefly, RNA was extracted from the growing cells by an SDS precipitation and organic solvent partition procedure. The RNA was transcribed using superscript reverse transcriptase and random hexamer primers. The same batch of reverse transcript was used for detection of all the growth factors. PCR was performed under standard conditions, using 4 μl reverse transcript, corresponding to 200 ng RNA in a total volume of 20 μl.

Based on this assay, acidic and basic FGF, TGF-α and TGF-β, and KGF mRNA transcripts were present as were several others as shown in Table III, including PDGF, amphiregulin, HBEGF, IGF, SPARC and VEGF. Of these, PDGF and TGF-β3 are thought to be involved in regulation of cell proliferation and matrix deposition in culture, while TGF-β1, HBEGF, KGF, SPARC, VEGF and decorin are deposited in the matrix. Amphiregulin, IGF-1, IGF-2 and IL-1 were not expressed at the sensitivity used in these experiments.

TABLE III

| Messenger RNA | Full Name | Function | Expression |
|---|---|---|---|
| PDGF-A Chain | Platelet-derived growth factor, A chain | Mitogen for fibroblasts, granulation tissue, chemotactic | ++ |
| PDGF-B Chain | Platelet-derived growth factor, B chain | Mitogen for fibroblasts, granulation tissue, chemotactic | 0 – (+)* |
| IGF-1 | Insulin-like growth factor-1 | Mitogen for fibroblasts | 0 |
| IGF-2 | Insulin-like growth factor-2 | Mitogen for fibroblasts | (+) |
| TGF-α | Transforming growth factor-α | Mitogen for fibroblasts, keratinocytes | + |
| Amphiregulin | Amphiregulin | Mitogen for fibroblasts, keratinocytes | 0 |
| KGF | Keratinocyte growth factor | Mitogen for keratinocytes | ++ |
| HBEGF | Heparin-binding epidermal growth factor-like growth factor | Mitogen for fibroblasts, keratinocytes | +++ |
| TGF-β1 | Transforming growth factor-β1 | Stimulates matrix deposition | + |
| TGF-β3 | Transforming growth factor-β3 | Stimulates matrix deposition | ++ – ++ |
| VEGF | Vascular endothelial growth factor | Angiogenic factor | ++ |
| SPARC | Secreted protein acidic and rich in cysteine | Complex anti-angiogenic, angiogenic | ++++ |
| ICAM-1 | Intercellular adhesion molecule-1 | Lymphocyte adhesion, mobility | + |
| VCAM | Vascular cellular adhesion molecule | Lymphocyte adhesion, mobility | +++ |
| GAPDh | Glyceraldehyde 3-phosphate dehydrogenase | Glycolytic housekeeping gene | +++ |
| β2-microglobulin | β2-microglobulin | Antigen presentation | +++ |

°A small amount of PDGF B chain is seen in some preparations.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A method for the repair of a skin defect comprising: injecting a human secreted extracellular matrix comprising a mixture of cell-free, naturally secreted human extracellular components derived from living stromal tissue formulated for in vivo administration by injection via a syringe and a pharmaceutically acceptable carrier at a site of a skin or tissue defect.

2. The method according to claim 1 in which the naturally secreted extracellular matrix is produced by a method comprising:

(a) providing a living stromal tissue prepared in vitro comprising human stromal cells and connective tissue proteins naturally secreted by the stromal cells attached to and substantially enveloping a framework, said framework composed of a biocompatible, non-living material formed into a three-dimensional structure having interstitial spaces bridged by the stromal cells;

(b) killing the cells in the living stromal tissue;

(c) removing the killed cells and any cellular contents from the framework;

(d) collecting the connective tissue proteins naturally secreted by the stromal cells attached to the framework; and (e) processing the collected connective tissue proteins of step (d) with a pharmaceutically acceptable carrier into a formulation that is suitable for in vivo administration by injection via a syringe.

3. The method according to claim 2 in which the collected connective tissue proteins of step (d) are processed by homogenizing, cross-linking, or suspending the collected connective tissue proteins in a physiological acceptable carrier prior to step (e).

4. The method according to claim 2 in which the collected connective tissue proteins of step (d) are processed by adjusting ratios of collagen types I–V, respective to each other, prior to step (e).

5. The method according to claim 2 in which the stromal cells of the living stromal tissue are fibroblasts.

6. The method according to claim 2 in which the stromal cells of the living stromal tissue are cells found in loose connective tissue or bone marrow.

7. The method according to claim 6 in which the stromal cells of the living stromal tissue are endothelial cells, pericytes, macrophages, monocytes, leukocytes, plasma cells, mast cells, chondrocytes or adipocytes.

8. The method according to claim 2 in which the framework is composed of a biodegradable material.

9. The method according to claim 8 in which the biodegradable material is cotton, polyglycolic acid, cat gut sutures, cellulose, gelatin, or dextran.

10. The method according to claim 2 in which the framework is composed of a non-biodegradable material.

11. The method according to claim 10 in which the non-biodegradable material is a polyamide, a polyester, a polystyrene, a polypropylene, a polyacrylate, a polyvinyl, a polycarbonate, a polytetrafluoroethylene, or a nitrocellulose compound.

12. The method according to claim 2, 3, 4, 5, 6, 7, 8, 9, 10 or 11 in which the framework is a mesh.

13. The method according to claim 12 in which the framework has pore spaces of about 150 $\mu$m to about 220 $\mu$m.

14. The method according to claim 2 in which the pharmaceutically acceptable carrier contains an anesthetic agent, a lubricating agent, a tissue growth factor or combinations thereof.

15. The method according to claim 1 in which the naturally secreted extracellular matrix is produced by a method comprising:

(a) providing a living stromal tissue prepared in vitro comprising human stromal cells and connective tissue proteins naturally secreted by the stromal cells attached to and substantially enveloping a framework, said framework composed of a biocompatible, non-living biodegradable material formed into a three-dimensional structure having interstitial spaces bridged by the stromal cells;

(b) killing the cells in the living stromal tissue;

(c) removing the killed cells and any cellular contents from the framework; and (d) processing the connective tissue proteins naturally secreted by the stromal cells attached to the framework and the biodegradable framework with a pharmaceutically acceptable carrier into a formulation suitable for in vivo administration by injection via a syringe.

16. The method according to claim 6 in which the stromal cells of the living stromal tissue are glial cells, liver cells, hematopoietic cells, dermal cells, lens fiber cells, smooth muscle cells, osteoblast cells, odontoblast cells, or retinal cells.

* * * * *

UNITED STATES PATENT AND TRADEMARK OFFICE
CERTIFICATE OF CORRECTION

PATENT NO.    : 6,284,284 B1
DATED         : September 4, 2001
INVENTOR(S)   : Gail K. Naughton It is certified that error appears in the above-identified patent and that said Letters Patent is hereby corrected as shown below:

<u>Title page,</u>
Item [56], OTHER PUBLICATIONS, in the "Oliver et al., 1980", reference "cross-liinking" should be -- cross-linking --.

<u>Column 1,</u>
Line 52, "collage n" should be -- collagen --.

<u>Column 11,</u>
Line 45, "depends" should be -- depend --.

<u>Column 12,</u>
Line 6, "crypreserved" should be -- cryopreserved --.

<u>Column 18,</u>
Line 43, after "periodicity" but before "in both preparations", insert -- were evident --.

<u>Column 20,</u>
Line 62, after "skin" but before "defect", insert -- or tissue --.
Line 63, after "human" but before "secreted", insert -- naturally --.

<u>Column 21,</u>
Line 25, "physiological" should be -- physiologically --.

Signed and Sealed this

Twenty-fifth Day of February, 2003

JAMES E. ROGAN
*Director of the United States Patent and Trademark Office*